US008450531B2

(12) United States Patent
Kondo et al.

(10) Patent No.: US 8,450,531 B2
(45) Date of Patent: May 28, 2013

(54) METHOD FOR SYNTHESIZING ACROLEIN

(75) Inventors: Takeyuki Kondo, Hitachi (JP);
Masayuki Kamikawa, Hitachinaka (JP);
Kenichiro Oka, Mito (JP); Toshiaki Matsuo, Mito (JP); Masashi Tanto, Tokyo (JP); Yasunari Sase, Tokyo (JP);
Hiroyuki Ito, Tokyo (JP); Tomofumi Shiraishi, Hitachi (JP); Tsutomu Kawamura, Mito (JP); Naruyasu Okamoto, Tokyo (JP)

(73) Assignee: Hitachi Plant Technologies, Ltd., Tokyo (JP)

( * ) Notice: Subject to any disclaimer, the term of this patent is extended or adjusted under 35 U.S.C. 154(b) by 217 days.

(21) Appl. No.: 12/979,459

(22) Filed: Dec. 28, 2010

(65) Prior Publication Data

US 2011/0160447 A1 Jun. 30, 2011

(30) Foreign Application Priority Data

Dec. 28, 2009 (JP) ................... 2009-297832

(51) Int. Cl.
*C07C 45/64* (2006.01)
*C07D 307/46* (2006.01)
*C07H 1/00* (2006.01)

(52) U.S. Cl.
USPC ............................ 568/491; 549/498; 536/124

(58) Field of Classification Search
USPC ............................ 568/491; 549/498; 536/124
See application file for complete search history.

(56) References Cited

U.S. PATENT DOCUMENTS

2008/0165616 A1 7/2008 Schubert et al.

FOREIGN PATENT DOCUMENTS

| JP | 10-212253 | 8/1998 |
|---|---|---|
| JP | 2006-167600 | 6/2006 |
| JP | 2008-012453 | 1/2008 |
| JP | 2009 132663 | 6/2009 |
| JP | 2010-013367 | 1/2010 |
| JP | 2010-046634 | 3/2010 |
| JP | 2010184897 | 8/2010 |
| WO | WO 2006/105870 | 10/2006 |

OTHER PUBLICATIONS

Watanabe et al., "Acrolein Synthesis From Glycerol in Hot-Compressed Water," Bioresource Technology 98, 2007, pp. 1285-1290.
Multi-Client Search Report, "1,3-PDO, PTT no Seizo, Yoto oyobi Keizai-sei (Production, Intended Use, and Economic Efficiency of 1,3-PDO, PTT)," 2000, CMC Publishing Co., Ltd., Planet Department.
Lehr et al., Catalytic Dehydration of Biomass-Derived Polyols in Sub- and Supercritical Water, Catalysis Today, vol. 121, No. 1-2, Feb. 13, 2007, pp. 121-129.
Ott et al., Catalytic Dehydration of Glycerol in Sub- and Supercritical Water: A new Chemical Process for Acrolein Production, Green Chemistry, Royal Society of Chemistry, vol. 8, No. 2, Jan. 1, 2006, pp. 214-220.
Bühler et al., Ionic Reactions and Pyrolysis of Glycerol as Competing Reaction Pathways in Near- and Supercritical Water, Journal of Supercritical Fluids, vol. 22, No. 1, Jan. 1, 2002.
Krammer et al., Untersuchungen Zum Synthesepotential in Ueberkritischem Wasser, Chemie Ingenieur Technik, vol. 70, No. 12, Dec. 1, 1998, pp. 1559-1563 with partial translation.
EP Search Report dated Apr. 1, 2011 in English.

*Primary Examiner* — Sikarl Witherspoon
(74) *Attorney, Agent, or Firm* — Antonelli, Terry, Stout & Kraus, LLP.

(57) ABSTRACT

An object of the present invention is to provide a method for commercially manufacturing acrolein in a large flow rate by making supercritical water and an acid interact with glycerin, wherein by efficiently mixing high-concentration glycerin and supercritical water with each other, the method is made capable of making the synthesis stably proceed with a high yield while the occlusion and abrasion of the pipes and devices due to the generation of by-products are being suppressed. The method for synthesizing acrolein of the present invention is a method for synthesizing acrolein by making supercritical water and an acid interact with glycerin, the method using a reaction apparatus including: a cylindrical mixing flow path for mixing a fluid including glycerin and a fluid including supercritical water with each other; a first inlet flow path, disposed offset from the central axis of the mixing flow path, for making the fluid including glycerin flow into the mixing flow path; and a second inlet flow path, disposed offset from the central axis of the mixing flow path, for making the fluid including supercritical water flow into the mixing flow path, wherein the first inlet flow path and the second inlet flow path are each provided in a plurality of numbers in such a way that the first inlet flow paths and the second inlet flow paths are alternately arranged so as to encircle the central axis of the mixing flow path.

13 Claims, 17 Drawing Sheets

METHOD FOR SYNTHESIZING ACROLEIN

BACKGROUND OF THE INVENTION

1. Field of the Invention

The present invention relates to a method for synthesizing an organic substance using supercritical water, in particular, a method for synthesizing acrolein, which is a raw material for 1,3-propanediol, from glycerin in the presence of proton.

2. Background Art

Recently, demand for 1,3-propanediol has been increased because 1,3-propanediol is a raw material for high quality polyester fibers including polytrimethylene terephthalate. One of the methods for synthesizing 1,3-propanediol is a method for hydrating and hydrogenating acrolein shown in "Production, applications and economic efficiency of 1,3-PDO and PTT, CMC Co., Ltd., Planet Division, August, 2000." This method produces 1,3-propanediol by hydration and hydrogenation reactions of acrolein obtained by air oxidation of propylene, which is a petroleum-based raw material, in the presence of a catalyst; this method is established as an industrial method. However, because of the recent increase in the price of crude oil, development of methods for synthesizing 1,3-propanediol from biological raw materials has been demanded.

There has not been reported any synthesis method of chemically synthesizing 1,3-propanediol from biological raw materials; however, there are techniques for synthesizing acrolein, which is a precursor of 1,3-propanediol, and examples of such techniques include a technique described in "WATANABE Masaru, IIDA Toru, AIZAWA Yuichi, AIDA Taku M, INOMATA Hiroshi, Acrolein synthesis from glycerol in hot-compressed water, Bioresource Technology 98, 1285-1290 (2007)." This method is a method in which, by using a small-scale apparatus such that the pipe diameter is of the order of 1 mm and the flow rate is 10 to 50 ml/min, an aqueous solution of glycerin as a biological raw material and high-temperature supercritical water are mixed with each other at 35 MPa, and thus the temperature of the resulting mixture is instantly increased to 400° C. to synthesize acrolein (the optimal reaction time is about 20 seconds). This method is characterized in that the proton originating from sulfuric acid added in a small amount to the aqueous solution of glycerin functions as a catalyst accelerating the dehydration reaction of glycerin. However, in "WATANABE Masaru, IIDA Toru, AIZAWA Yuichi, AIDA Taku M, INOMATA Hiroshi, Acrolein synthesis from glycerol in hot-compressed water, Bioresource Technology 98, 1285-1290 (2007)," the glycerin concentration in the raw material is as low as about 1%, and a large amount of energy is consumed for the temperature increase and pressure increase of water, and hence, for the purpose of commercial manufacturing, it is necessary to increase the glycerin concentration in the reaction solution to a high concentration of at least 15% or more.

However, when the glycerin concentration is increased to 15% or more, the reaction rate comes to be high and the optimal reaction time comes to be a few seconds, and hence complete mixing is required to be completed in at least 1/10th the reaction time. On the other hand, with the increase of the glycerin concentration, the viscosity difference between the supercritical water and the aqueous solution of glycerin is increased, and accordingly the miscibility therebetween is degraded. In particular, in a commercial plant of a size of a few ten thousands t/y, in the case where the reaction solutions are mixed at an economic flow speed, the pipe diameter comes to be about 1 to 10 cm, and concomitantly, the diffusion distance is also increased. In this connection, the mixing time is reciprocally proportional to the square of the pipe diameter, and hence the mixing time comes to be a few seconds or more. When the miscibility is degraded, the coordination number of the supercritical water in the vicinity of the glycerin molecules is degraded. FIG. 1 shows the dehydration reaction route of glycerin on the basis of the use of supercritical water. When the coordination number is decreased, the side reaction proceeds more predominantly than the main reaction to produce acrolein, and hence the reaction yield of acrolein is degraded. Additionally, with the decrease of the miscibility, glycerin is brought into contact with supercritical water to react with supercritical water at a temperature higher than the optimal reaction temperature, and hence the amounts of the generated reaction by-products such as tar and carbon particles are increased to further decrease the yield. The carbon particles aggregated with the aid of tar adhere to the valving elements and valve seats. Consequently, abrasion or the like of the valving elements and the valve seats occurs, and the operation ranges of the valving elements are limited to lead to a possibility that precise pressure control is made difficult. Therefore, from the viewpoints of the increase of the glycerin concentration and the scale-up of the reaction, the improvement of the miscibility is required.

In JP Patent Publication (Kokai) No. 2006-167600, a method for improving the miscibility is reported. In this method, the introduction pipe of a first fluid and the introduction pipe of a second fluid are connected to the mixing pipe under the condition that the central axis of the introduction pipe of the first fluid and the central axis of the introduction pipe of the second fluid are deviated from each other, and thus swirl flow is generated in the mixing pipe to thereby improve the miscibility. However, the number of the introduction pipes is small, and hence a high miscibility is obtained with the thin pipe of the order of millimeters in the diameter of the mixing pipe, but in a case of a commercial plant of the order of a few ten thousands t/y having a mixing pipe diameter of the order of 10 cm, no sufficient miscibility is obtained.

On the other hand, in the high-temperature, high-pressure micromixer described in JP Patent Publication (Kokai) No. 2008-12453, a first reaction solution is introduced into the central axis of a mixing pipe and two introduction pipes of a second reaction solution are disposed at the positions offset from the central axis, and hence there is a problem that a multiple layer flow is hardly formed and the mixing time is made long.

SUMMARY OF THE INVENTION

An object of the present invention is to provide a method for commercially manufacturing acrolein in a large flow rate by making supercritical water and an acid interact with glycerin, wherein by efficiently mixing high-concentration glycerin and supercritical water with each other, the method is made capable of making the synthesis stably proceed with a high yield while the occlusion and abrasion of the pipes and devices due to the generation of by-products are being suppressed.

The present invention is characterized in that, for the purpose of solving the above-described problems, in a method for synthesizing acrolein by making supercritical water and an acid interact with glycerin, the method uses a reaction apparatus including: a cylindrical mixing flow path for mixing a fluid containing glycerin and a fluid containing supercritical water with each other; a first inlet flow path, disposed offset from the central axis of the mixing flow path, for making the fluid containing glycerin flow into the mixing flow path; and a second inlet flow path, disposed offset from the central axis of the mixing flow path, for making the fluid containing supercritical water flow into the mixing flow path, wherein the first inlet flow path and the second inlet flow path are each provided in a plurality of numbers in such a way that the first inlet flow paths and the second inlet flow paths are alternately arranged so as to encircle the central axis of the mixing flow path. Here, applicable as the acid are sulfuric acid, diluted sulfuric acid, solid acid catalysts and the like.

The present invention is also characterized in that in a method for synthesizing acrolein by making supercritical water and an acid interact with glycerin, the method uses a reaction apparatus including: a cylindrical mixing flow path for mixing a fluid containing glycerin and a fluid containing supercritical water with each other; a first inlet flow path, disposed offset from the central axis of the mixing flow path, for making the fluid containing glycerin flow into the mixing flow path; and a second inlet flow path, disposed offset from the central axis of the mixing flow path, for making the fluid containing supercritical water flow into the mixing flow path, wherein the first inlet flow path and the second inlet flow path are each provided in a plurality of numbers along the flow direction of the mixing flow path so as to be separated away from each other.

The present invention is also characterized in that a structure is disposed on the central axis of the mixing flow path.

The present invention is also characterized in that the structure disposed on the central axis of the mixing flow path is formed in such a way that the cross sectional area of the structure is made smaller toward the downstream of the mixing flow path.

The present invention is also characterized in that between the flow rate $Q_X$ and the cross sectional area $S_X$ per one of the first inlet flow paths and the flow rate $Q_Y$ and the cross sectional area $S_Y$ per one of the second inlet flow paths, the relation represented by the formula (1) is satisfied, and the flow speeds at the inlet flow paths are equal to each other.

$$Q_X/S_X = Q_Y/S_Y \quad (1)$$

The present invention is also characterized in that the method for synthesizing acrolein performs the synthesis by installing in combination a plurality of such reaction apparatuses as described above.

The present invention is also characterized in that in a method for synthesizing acrolein by making supercritical water and an acid interact with glycerin, the method uses a reaction apparatus including: a cylindrical mixing flow path for mixing a fluid containing glycerin and a fluid containing supercritical water with each other; a first inlet flow path, connected to the mixing flow path, for making the fluid containing glycerin flow into the mixing flow path; and a second inlet flow path, connected to the mixing flow path, for making the fluid containing supercritical water flow into the mixing flow path, wherein a static mixer is disposed in the mixing flow path.

The present invention is also characterized in that in a method for synthesizing acrolein by making supercritical water and an acid interact with glycerin, the method uses a reaction apparatus including: a cylindrical mixing flow path for mixing a fluid containing glycerin and a fluid containing supercritical water with each other; a first inlet flow path, connected to the mixing flow path, for making the fluid containing glycerin flow into the mixing flow path; and a second inlet flow path, connected to the mixing flow path, for making the fluid containing supercritical water flow into the mixing flow path, wherein a perforated plate is disposed in the mixing flow path.

The present invention is also characterized in that in a method for synthesizing at least one selected from acrolein, glucose and hydroxymethylfurfural by making at least one of supercritical water and subcritical water interact with a raw material containing at least one selected from glycerin, cellulose and lignin, the method uses a reaction apparatus including: a cylindrical mixing flow path for mixing a fluid containing the raw material and a fluid containing at least one of supercritical water and subcritical water with each other; a first inlet flow path, disposed offset from the central axis of the mixing flow path, for making the fluid containing the raw material flow into the mixing flow path; and a second inlet flow path, disposed offset from the central axis of the mixing flow path, for making the fluid containing at least one of supercritical water and subcritical water flow into the mixing flow path, wherein the first inlet flow path and the second inlet flow path are each provided in a plurality of numbers in such a way that the first inlet flow paths and the second inlet flow paths are alternately arranged so as to encircle the central axis of the mixing flow path.

According to the present invention, the fluid containing glycerin and the fluid containing supercritical water can be mixed with each other in the mixing flow path with the aid of swirl flow, and at the same time, two different types of fluids can be made to flow in multiple layers (preferably, each fluid is made to flow in four directions to form swirl flow, and thus in optimal eight layers), and hence the diffusion distance between the two types of fluids can be reduced, and the miscibility can be improved.

Because a structure is disposed on the central axis of the mixing flow path, no mixing solutions are made to present in the vicinity of the central axis. Although the mixing with the aid of swirl flow generates a partial region low in miscibility on the central axis of the mixing flow path, the above-described contrivance suppresses the occurrence of such a region to improve the miscibility. Additionally, by disposing the structure, the distance between the mixing flow path and the structure is made small and the interlayer distances in the multiple layer flow are reduced and hence the miscibility can be improved.

Additionally, because a plurality of the reaction apparatuses utilizing swirl flow are installed in combination (numbering-up), the miscibility improvement and the pressure reduction can be made compatible with each other.

Such a miscibility improving measure as described above enables a commercial plant of a scale of 100,000 t/y, in which the inner diameter of the mixing pipe is large, to attain a sufficient miscibility, and hence the reaction yield is improved and the amounts of generated tar and the generated by-products can be reduced. Accordingly, the occlusion of the pipes and valves due to the adhesion of the by-products can be prevented. Further, the abrasion of the valving elements and the valve seats are suppressed, and hence the precise pressure control can be performed. Therefore, highly efficient operation of the commercial plant is made possible.

The constitution of the present invention as described above can be applied not only to the case where the raw material is glycerin but also to the case where other biomass resources such as cellulose and lignin are used as the raw materials and are made to react with supercritical water or subcritical water. In this regard, it is preferable that the raw materials such as cellulose and lignin be mixed, before being subjected to the reaction, with subcritical water offering relatively mild conditions and be dissolved in subcritical water. In the case where cellulose is used as the raw material, by making subcritical water being smaller in the action of proton (decomposition action) in place of supercritical water and a dehydrating agent such as acetic anhydride in place of sulfuric acid interact with cellulose, glucose and hydroxymethylfurfural (one of the intermediates of medicinal chemicals) are synthesized. In the case where lignin is used as the raw material, by making the oxidant such as hydrogen peroxide in place of subcritical water and sulfuric acid interact with lignin, succinic acid (one of the raw materials for polybutylene succinate, a bioplastic) is synthesized. In each case, by improving the miscibility between subcritical water and the raw material on the basis of the present invention, the yield improvement and the prevention of the drawbacks such as the occlusion due to the by-products can be realized.

DESCRIPTION OF SYMBOLS

Figure 1:
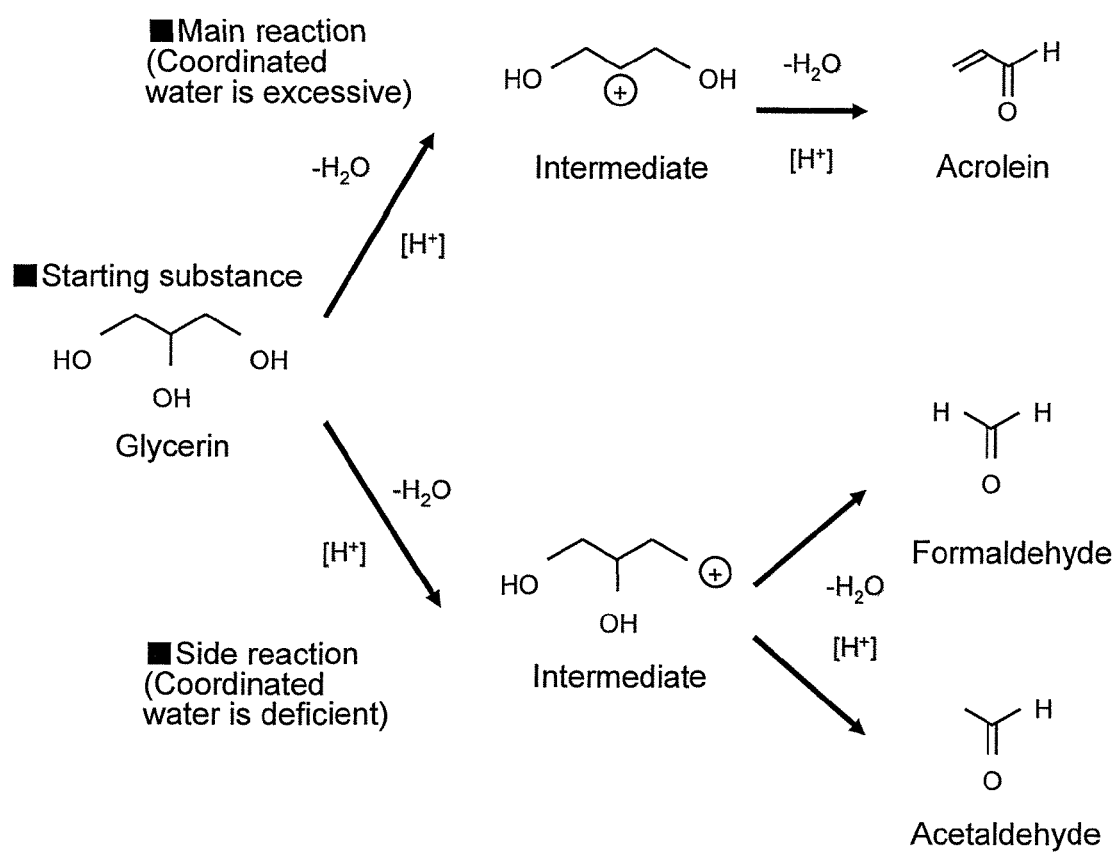
FIG. 1 is a diagram showing the dehydration reaction path of glycerin using supercritical water.

100: Water header
110: Supercritical water high pressure pump
120: Supercritical water pre-heater
200: Raw material header
210: Raw material high pressure pump
220: Raw material pre-heater
300, 300a, 300b: Reaction apparatus
310X: First inlet flow path
310Y: Second inlet flow path
320: Mixing flow path
325: Structure
326: Static mixer
327: Perforated plate
330: Mixing flow path outlet
400: Cooling water header
410: Cooling water high pressure pump
420a, 420b: Junction of reaction solution and cooling water
500a, 500b: Backwashing fluid header
510a, 510b: Drain
520a, 520b: Filter
521a, 521b: Reaction solution inlet valve of filter
522a, 522b: Reaction solution outlet valve of filter
523a, 523b: Backwashing fluid inlet valve of filter
524a, 524b: Drain valve of filter
620: Cooler
630: Orifice
640: Pressure control valve
X: Raw material line
Y: Supercritical water line

DETAILED DESCRIPTION OF THE PREFERRED EMBODIMENTS

First Embodiment

Hereinafter, with reference to the accompanying drawings, description is made on the operation flow in which glycerin is selected as a raw material and supercritical water is selected as water, a reaction is started by mixing these, by-products are separated and removed, and then the reaction solution is collected.

Figure 2:
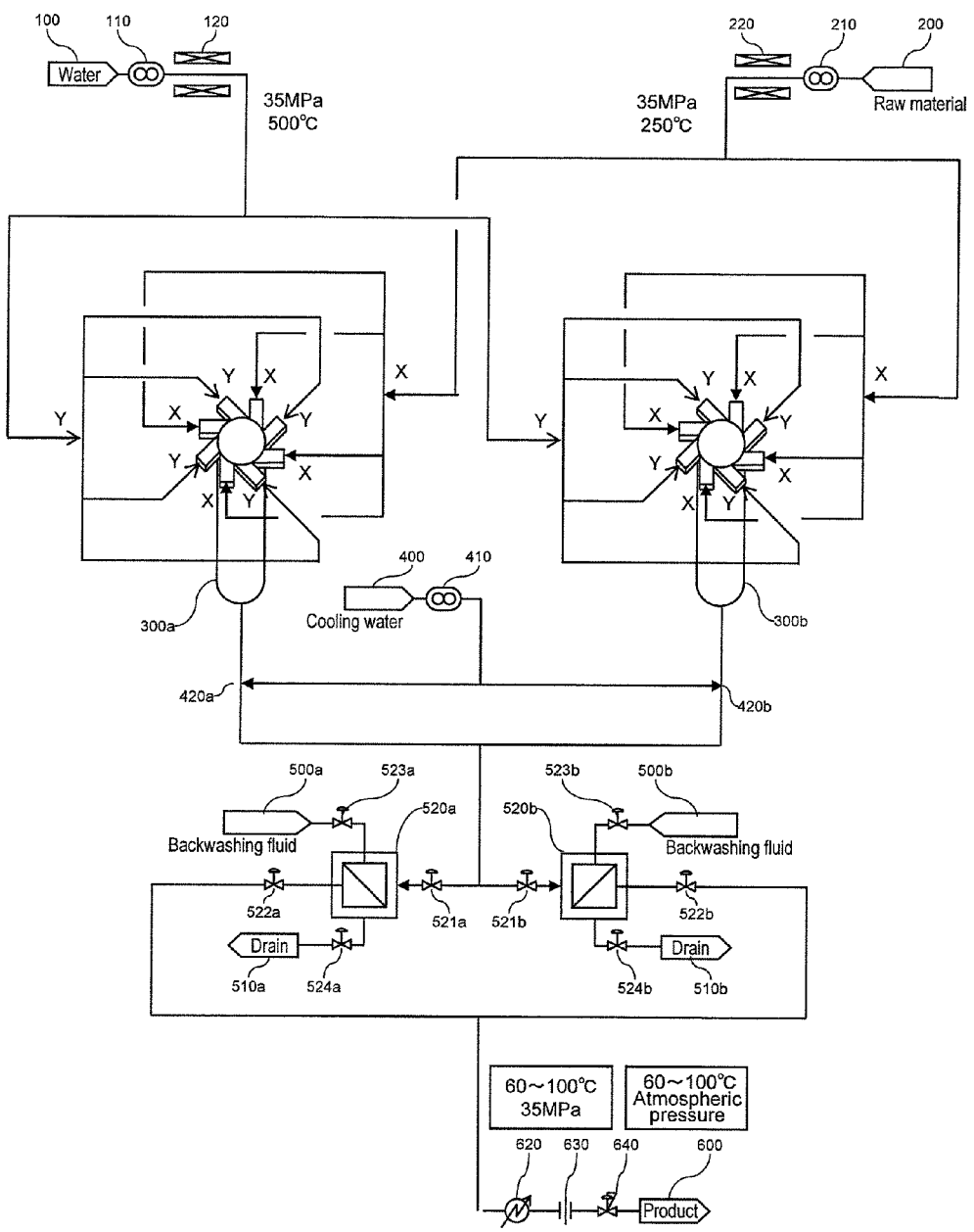
FIG. 2 is a view illustrating an embodiment of an apparatus for synthesizing acrolein, using supercritical water.

FIG. 2 is a view illustrating an embodiment of an apparatus for synthesizing acrolein, used in the present invention. First, water is delivered at 35 MPa with a supercritical water high pressure pump (110) and is increased in temperature to 500° C. with a supercritical water pre-heater (120). A raw material composed of glycerin and diluted sulfuric acid is delivered at 35 MPa with a raw material high pressure pump (210) and is increased in temperature to 250° C. with a raw material pre-heater (220). The water and the raw material are mixed with each other with reaction apparatuses (300a, 300b) utilizing swirl flow, and thus instantly the synthesis reaction of acrolein is started at 400° C. and 35 MPa.

Figure 3:
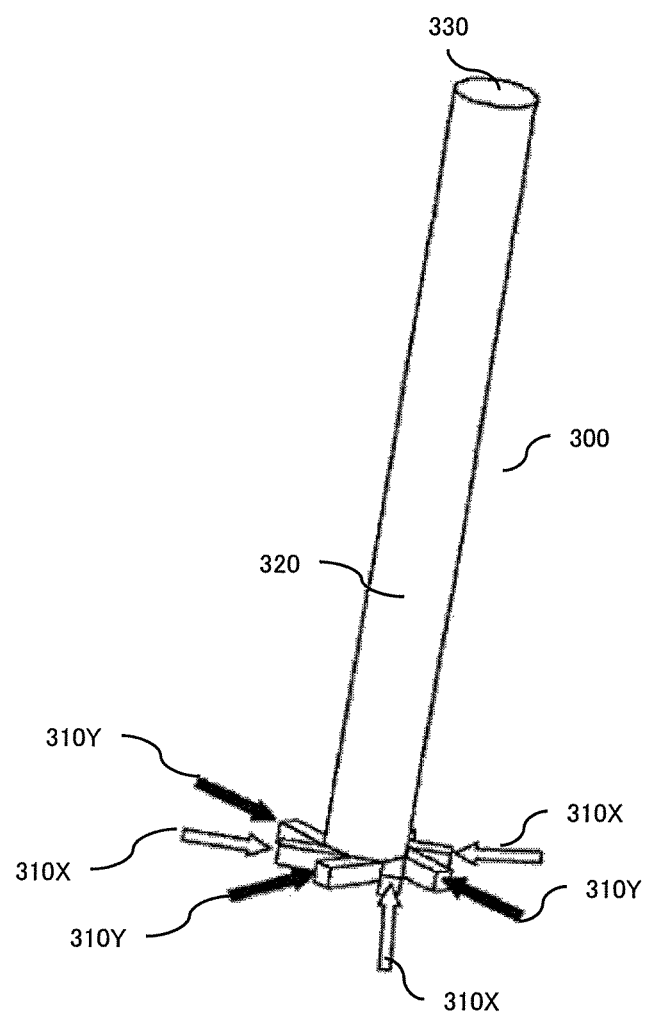
FIG. 3 is an oblique perspective view of a reaction apparatus utilizing swirl flow in the present invention.
Figure 4:
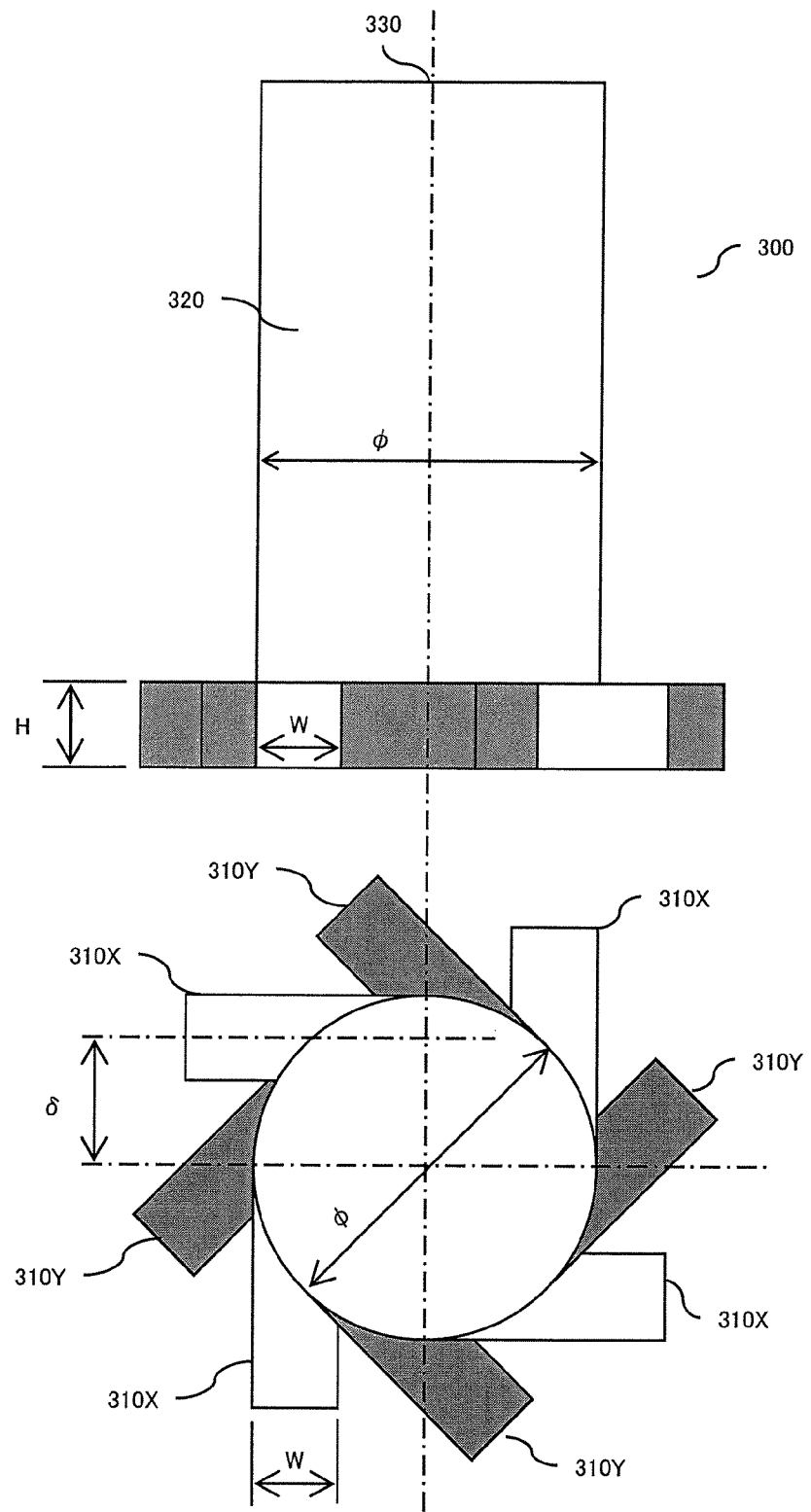
FIG. 4 is a front view and a plan view of a reaction apparatus utilizing swirl flow in the present invention.

FIG. 3 shows an oblique perspective view of a reaction apparatus utilizing swirl flow in the present invention, and FIG. 4 shows a front view and a plan view of the reaction apparatus shown in FIG. 3. The end of a cylindrical mixing flow path (320) is hermetically sealed, and first inlet flow paths (310X) for introducing a fluid containing glycerin into the mixing flow path (320) and second inlet flow paths (310Y) for introducing a fluid containing supercritical water into the mixing flow path (320) are connected to the hermetically sealed end. The first inlet flow paths (310X) and the second inlet flow paths (310Y) are each connected to the mixing flow path (320) in a condition of being offset by δ in relation to the central axis of the mixing flow path (320). With this structure, a swirl flow can be generated in the mixing flow path (320) and thus the miscibility can be improved.

Additionally, the first inlet flow paths (310X) and the second inlet flow paths (310Y) are connected in such a way that the total number of the inlet flow paths is eight, and the first and second inlet flow paths are alternately arranged so as to encircle the central axis of the mixing flow path (320) with a constant angular interval of 45°. A plurality of the first inlet flow paths (310X) and a plurality of the second inlet flow paths (310Y) are connected to the mixing flow path (320), hence a multiple layer flow can be formed in the mixing flow path (320), the diffusion distance is reduced as compared to the conventional two layer flow, and the miscibility can be improved.

In each of FIGS. 3 and 4, the first inlet flow paths (310X) and the second inlet flow paths (310Y) are connected at right angle to the central axis of the mixing flow path (320); however, the connection angle is not limited to this angle. By setting the connection angle at 90° or less, the flow direction in the mixing flow path (320) and the flow directions of the first and second inlet flow paths (310X, 310Y) come closer together, and hence the pressure loss can be reduced and the amount of production can be increased.

In FIG. 3 and the like, the cross sections of the first and second inlet flow paths (310X, 310Y) are depicted so as to be rectangles, but the first and second inlet flow paths (310X, 310Y) may have other shapes such as cylinders. The mixing flow path (320) is also assumed to have a cylindrical shape, and the cylindrical shape as referred to herein includes the shapes each having a polygonal cross section to be approximated as a circle. By setting the width W of each of the first and second inlet flow paths (310X, 310Y) at one fourth the diameter $\phi$ of the mixing flow path (320), the highest miscibility is obtained.

Figure 5:
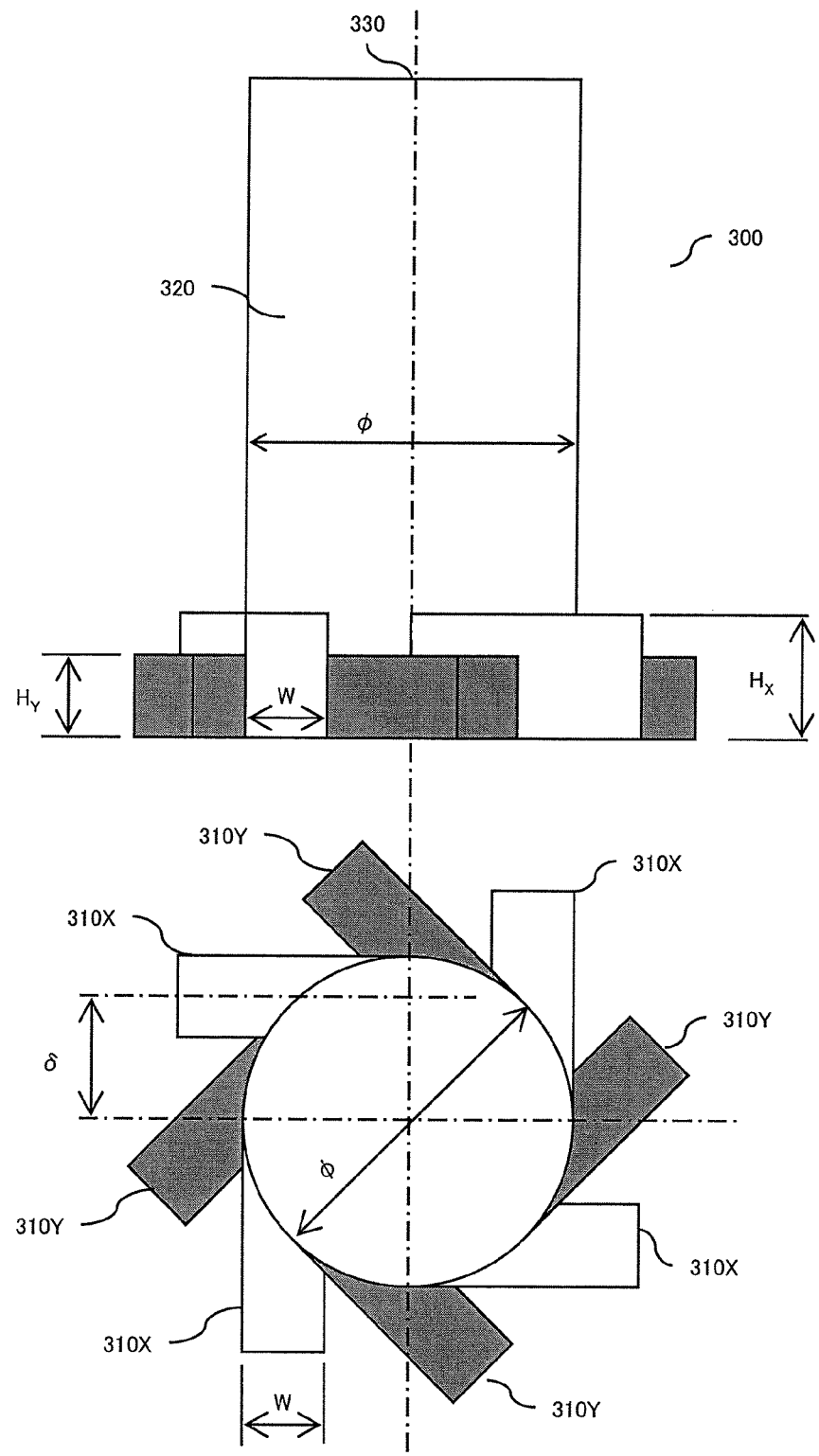
FIG. 5 is a front view and a plan view of a reaction apparatus utilizing swirl flow in the present invention.

Additionally, for the purpose of enhancing the miscibility in the mixing flow path (320), the flow rate $Q_X$ of the raw material high pressure pump (210) and the flow rate $Q_Y$ of the supercritical water high pressure pump (110) are preferably equal to each other. However, as shown in FIG. 5, when these two flow rates are different from each other, the miscibility can be improved by making the dimension of the first inlet flow paths (310X) and the dimension of the second inlet flow paths (310Y) different from each other in such a way that the flow speed in the first inlet flow paths (310X) and the flow speed in the second inlet flow paths (310Y) are equal to each other. In other words, the flow rate $Q_X$ and the cross sectional area $S_X$ expressed by W×$H_X$ of the first inlet flow path (310X) and the flow rate $Q_Y$ and the cross sectional area $S_Y$ expressed by W×$H_Y$ of the second inlet flow path (310Y) are preferably set to satisfy the relation $Q_X/S_X=Q_Y/S_Y$.

Figure 6:
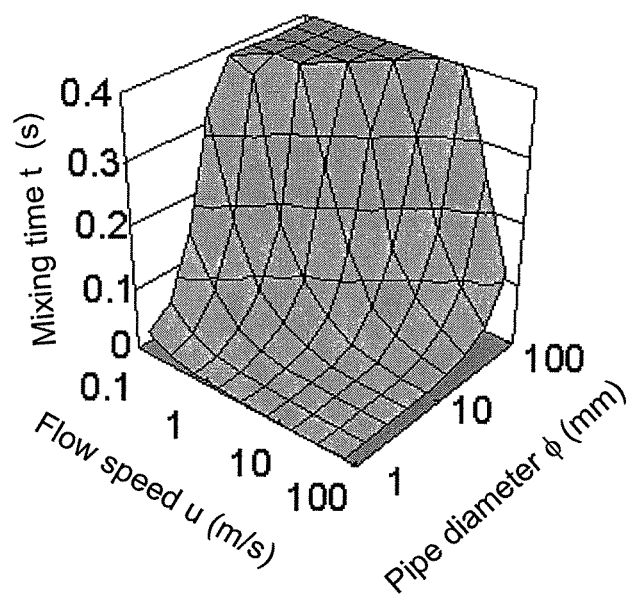
FIG. 6 is a graph showing the dependence of the mixing time on the flow speed and the pipe diameter in a mixing pipe.
Figure 7:
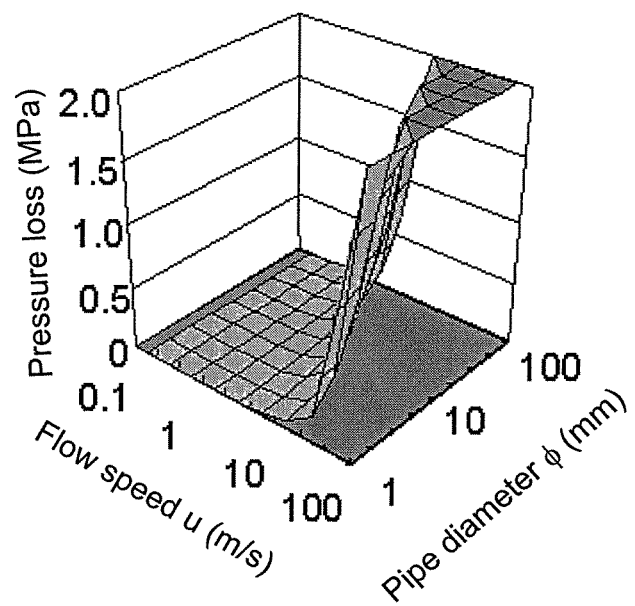
FIG. 7 is a graph showing the dependence of the pressure loss on the flow speed and the pipe diameter in a mixing pipe.
Figure 8:
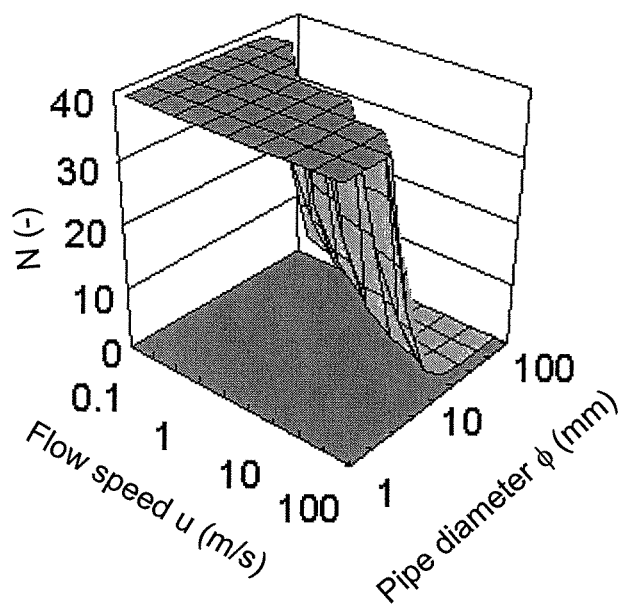
FIG. 8 is a graph showing the dependence of the numbering-up number N(−) on the flow speed and the pipe diameter in a mixing pipe.

When the flow speed is increased by making thin the inner diameter of the mixing flow path (320), the miscibility is improved to decrease the mixing time, but on the other hand, the pressure loss is increased; therefore, there are optimal values for the inner diameter of the pipe involved and the flow speed. FIGS. 6, 7 and 8 show the effects of the inner diameter $\phi$ of the mixing pipe and the flow speed u on the mixing time and the pressure loss in the mixing pipe and on the number N of the numbering up of the mixing pipe, in a case where the amount of production of acrolein is about 100,000 t/y. In the reaction of the present invention, from the viewpoints of the reaction yield improvement and the reduction of the amounts of the generated by-products, the mixing time is required to be set at 0.2 second or less. Additionally, in general, from the viewpoints of the reduction of the solution delivery energy and the reliability improvement of the instrumentation and control of the plant, the pressure loss and the number of the numbering up are required to be set at 1 MPa or less and 30 or less, respectively. In consideration of what has been described above, preferably the inner diameter of the mixing pipe is 10 to 50 mm, the flow speed is 2 to 20 m/s and the number of the numbering up is 10 to 50. Additionally, in a more preferable case, the inner diameter of the mixing pipe is about 20 mm, the flow speed is about 10 m/s and the number of the numbering up is about 30.

The material of the reaction apparatus of the present embodiment is preferably Ni-base alloys, having corrosion resistance equal to or higher than the corrosion resistance of SUS 316L, such as Inconel 625 and Hastelloy C-276.

By using the reaction apparatus shown in FIG. 3, even in a commercial plant having an amount of production of 100,000 t/y, the fluid containing supercritical water and the fluid containing glycerin are made to form multiple layers and the diffusion distance can be reduced, and by delivering the solutions with the aid of turbulent flow to increase the turbulent flow diffusion coefficient, the swirl flow can be generated in the mixing flow path; therefore, as a result of the combination of these facts, the miscibility can be drastically improved. By improving the miscibility, the reaction yield is improved and the amounts of generated tar and the generated by-products can be reduced. Accordingly, the occlusion of the pipes and valves due to the adhesion of the by-products can be prevented. Further, the abrasion of the valving elements and the valve seats are suppressed, and hence the precise pressure control can be performed. Therefore, highly efficient operation of the commercial plant is made possible.

Next, after the optimal reaction time has elapsed in the reaction apparatus (300), cooling water is delivered to the junction (420a, 420b) for the purpose of terminating the reaction by using the cooling water high pressure pump (410) shown in FIG. 2, and the reaction is terminated by direct mixing of the cooling water. Because the optimal reaction time is a few seconds when the glycerin concentration is set at 15%, the reaction solution is required to be rapidly cooled to the reaction termination temperature in a time of about one-tenth the optimal reaction time. Because the inner diameter of the reaction pipe is as large as a few centimeters, the adoption of the direct mixing of cooling water improves the controllability of the reaction time as compared to the indirect cooling with a double pipe cooler. Additionally, by using the above-described reaction apparatus utilizing swirl flow in order to mix the reaction solution and the cooling water with each other, the controllability of the reaction time is further improved and the reaction yield can be enhanced.

After the termination of the reaction, the reaction solution is subjected to the separation of tar and carbon particles with the filters (520a, 520b) in the subsequent stage in such a way that only the carbon particles are captured with the filters and the tar is allowed to pass while keeping the high viscosity thereof. Accordingly, the occlusion of the pipes due to the mutual aggregation of tar and carbon particles is prevented.

By preparing two or more systems of filters for separating and removing carbon particles, the operations of eliminating carbon particle cakes from these filter systems with the aid of backwashing can be performed alternately. Accordingly, not the whole plant is required to be halted, the continuous operability is improved, the heat loss due to the start-up of the plant can be reduced, and the operation cost can be reduced.

The reaction solution from which carbon particles have been removed is cooled in a second cooler (620), then decreased in pressure down to the atmospheric pressure with an orifice (630) and a pressure regulation valve (640) and is delivered to a distillation apparatus for acrolein in the subsequent stage.

Second Embodiment

Figure 9:
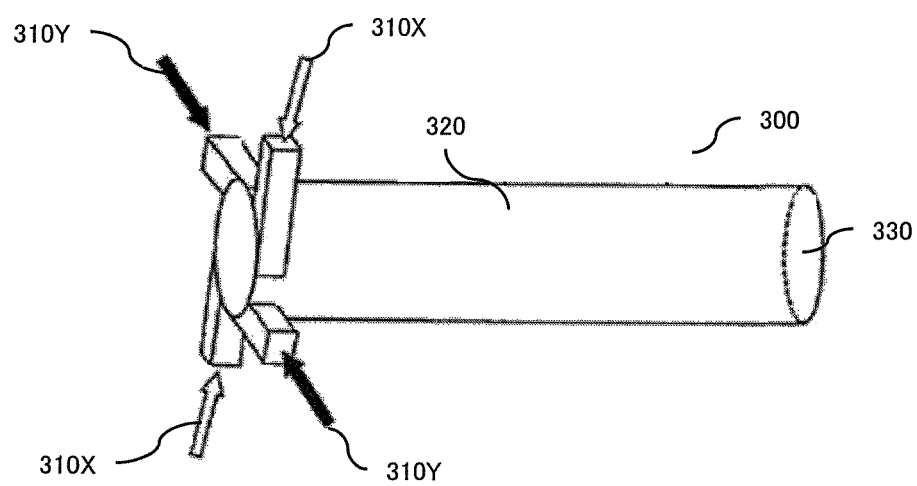
FIG. 9 is an oblique perspective view of a reaction apparatus utilizing swirl flow in the present invention.
Figure 10:
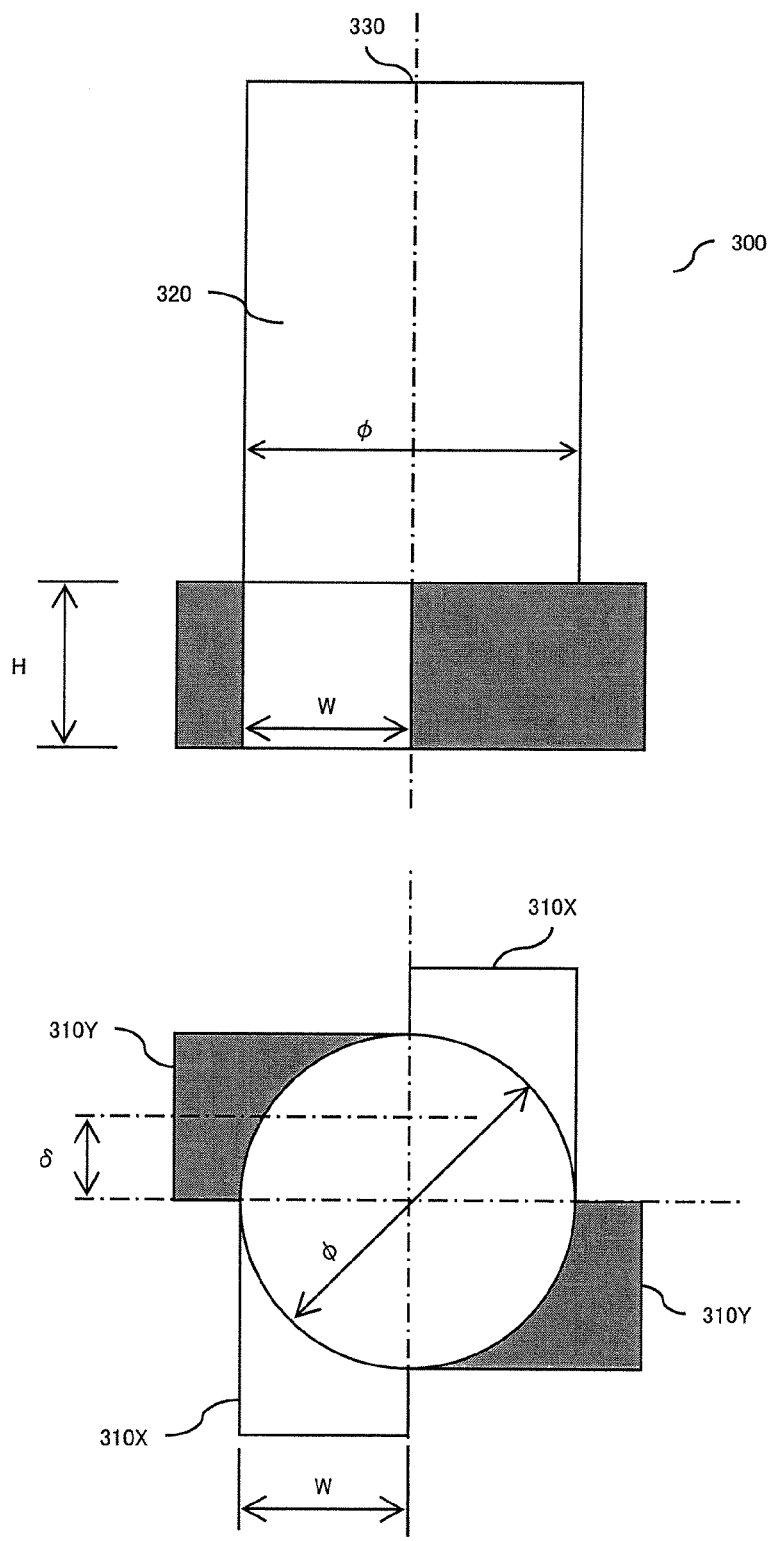
FIG. 10 is a front view and a plan view of a reaction apparatus utilizing swirl flow in the present invention.

FIG. 9 shows an oblique perspective view of an embodiment of the reaction apparatus utilizing swirl flow in the present invention, and FIG. 10 shows a front view and a plan view of the reaction apparatus. In the case of a small reaction apparatus having a mixing flow path (320) of 1 cm or less in inner diameter, eight of the first and second inlet flow paths (310X, 310Y) cannot be connected. In the reaction apparatus of the present embodiment, the first inlet flow paths (310X) and the second inlet flow paths (310Y) are connected in such a way that the total number of the inlet flow paths is four, and the first and second inlet flow paths are alternately arranged so as to encircle the central axis of the mixing flow path (320) with a constant angular interval of 90°. Although not shown, the total number of the first inlet flow paths (310X) and the second inlet flow paths (310Y) may also be six. The miscibility can be improved as compared to conventional T-shaped pipes and conventional reaction apparatuses having two inlet flow paths and utilizing swirl flow.

Third Embodiment

Figure 11:
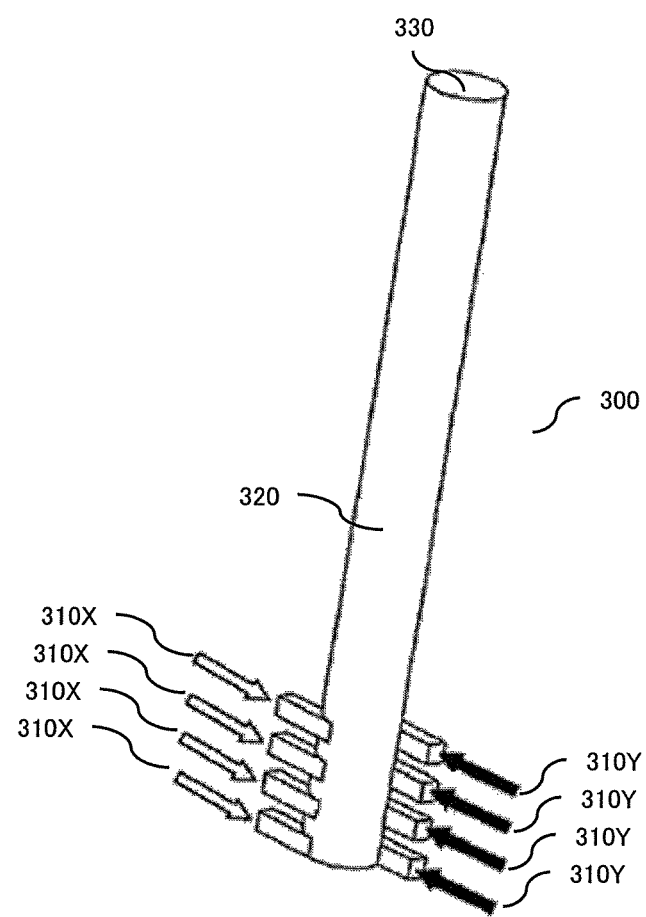
FIG. 11 is an oblique perspective view of a reaction apparatus utilizing swirl flow in the present invention.
Figure 12:
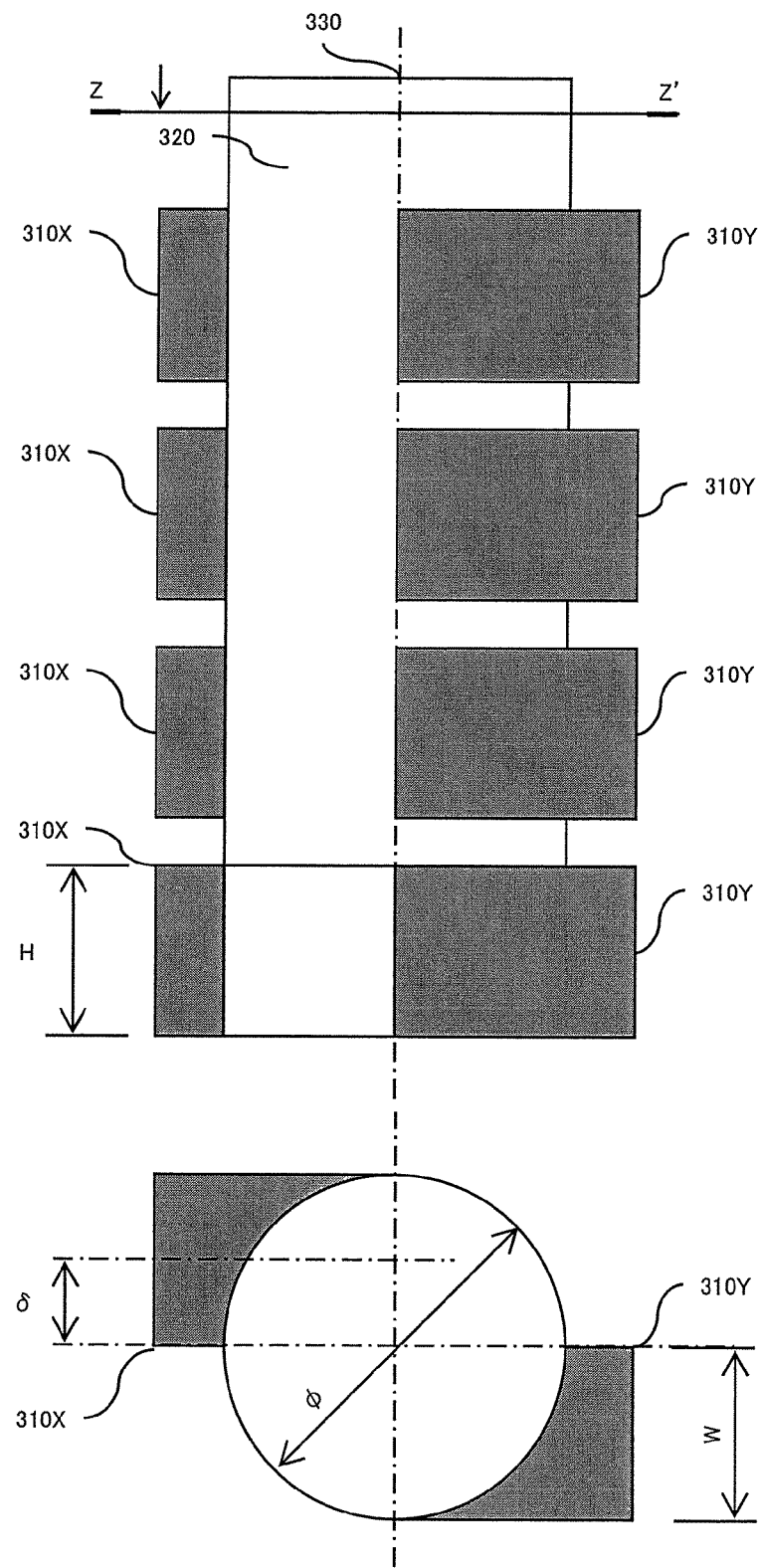
FIG. 12 a front view and a plan view of a reaction apparatus utilizing swirl flow in the present invention.
Figure 13:
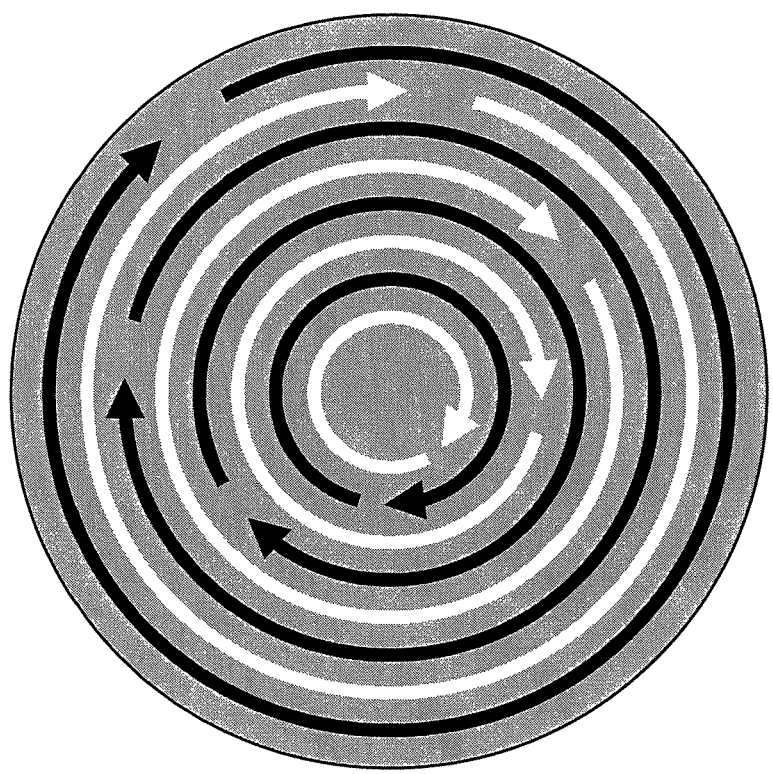
FIG. 13 is a Z-Z' cross sectional view of the mixing flow path in FIG. 12.

FIG. 11 shows an oblique perspective view of an embodiment of the reaction apparatus utilizing swirl flow in the present invention, and FIG. 12 shows a front view and a plan view of the reaction apparatus. In the reaction apparatus in the present embodiment, the end of the cylindrical mixing flow path (320) is hermetically sealed, and the first inlet flow paths (310X) for introducing a fluid containing glycerin into the mixing flow path (320) and the second inlet flow paths (310Y) for introducing a fluid containing supercritical water into the mixing flow path (320) are connected to the hermetically sealed end. The first inlet flow paths (310X) and the second inlet flow paths (310Y) are each connected to the mixing flow path (320) in a condition of being offset by δ in relation to the central axis of the mixing flow path (320). Additionally, the first inlet flow path (310X) and the second inlet flow path (310Y) are each provided in a plurality of numbers so as to be separated away from each other along the flow direction of the mixing flow path (320). Because the first inlet flow path and the second inlet flow path are each provided in a plurality of numbers so as to be separated away from each other along the flow direction, the swirl flow layer of the subsequent stage is generated outside the swirl flow layer of the preceding stage. Therefore, as shown in the Z-Z' cross section (FIG. 13) of the mixing flow path (320) shown in FIG. 12, a multiple layer swirl flow can be generated. Accordingly, the interlayer distances are reduced, and hence the miscibility can be improved. When the flow rate of the raw material high pressure pump and the flow rate of the supercritical water high pressure pump are different from each other, the miscibility can be enhanced, as described above, by determining the cross sectional area (W×H) of the first inlet flow path and the cross sectional area (W×H) of the second inlet flow path in such a way that the flow speed of the first inlet flow path and the flow speed of the second inlet flow path are equal to each other. In the present embodiment, the total number of the first and second inlet flow paths at each stage is set at 2; however, by increasing this total number to 4, 6 or 8, the miscibility can be further improved.

Fourth Embodiment

Figure 14:
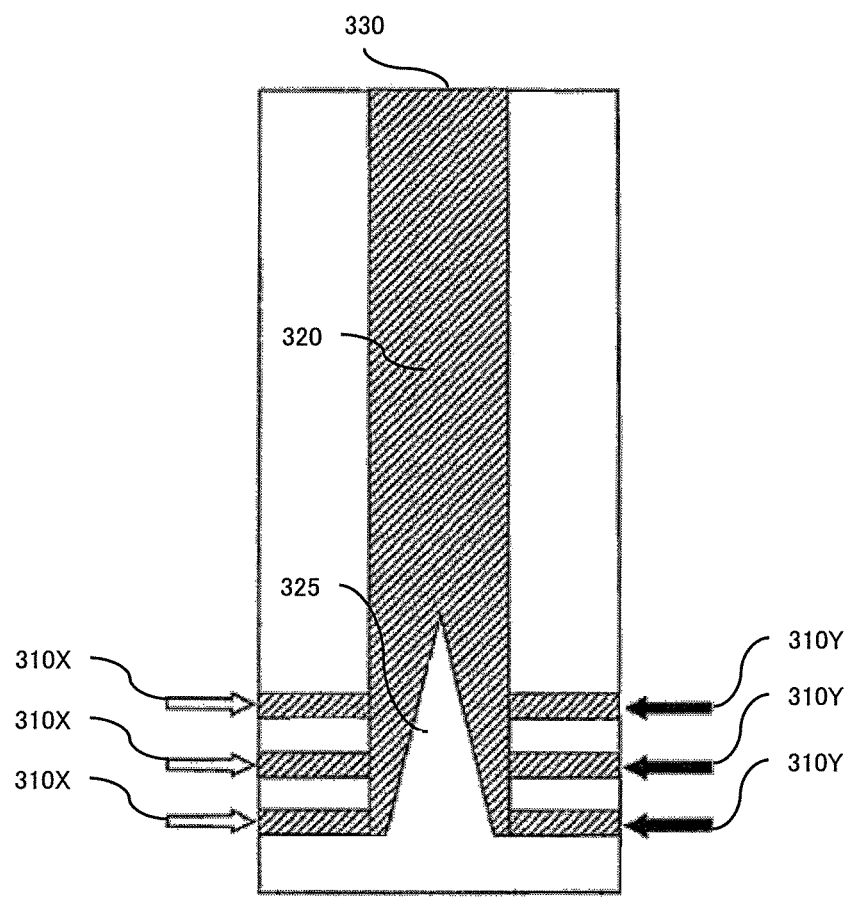
FIG. 14 is a cross sectional view of a reaction apparatus utilizing swirl flow in the present invention.

FIG. 14 shows an embodiment of the reaction apparatus utilizing swirl flow in the present invention. In the reaction apparatus utilizing swirl flow, a conical portion low in miscibility is generated on the central axis of the mixing flow path (320). The miscibility can be improved by disposing a structure (325) in the low miscibility portion. Additionally, by the presence of a structure in the central portion of FIG. 13, the interlayer distances are further reduced, and hence the miscibility can be improved. The structure disposed on the central axis of the mixing flow path is preferably formed so as to be made thinner (so as for the cross sectional area of the structure to be made smaller) as going toward the downstream of the mixing flow path. The use of the structure in the reaction apparatuses utilizing swirl flow of the other embodiments can also improve the miscibility.

Fifth Embodiment

Figure 15:
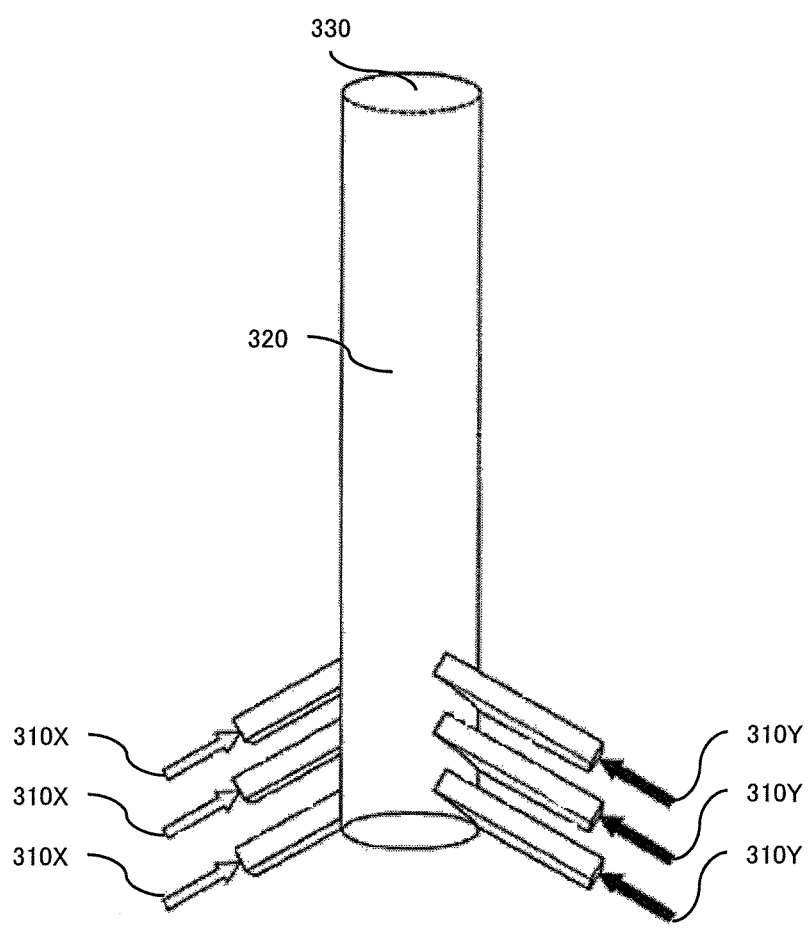
FIG. 15 is an oblique perspective view of a reaction apparatus utilizing swirl flow in the present invention.

FIG. 15 shows another embodiment of the reaction apparatus utilizing swirl flow in the present invention. For the purpose of improving the amount of production of the reaction apparatus, the throughput as well as the reaction yield is required to be increased. In the reaction apparatus in the present embodiment, the first and second inlet flow paths (310X, 310Y) are connected so as to make an angle of less than 90° relative to the central axis of the mixing flow path (320), and hence the pressure loss can be reduced and the amount of production can be increased.

Sixth Embodiment

Figure 16:
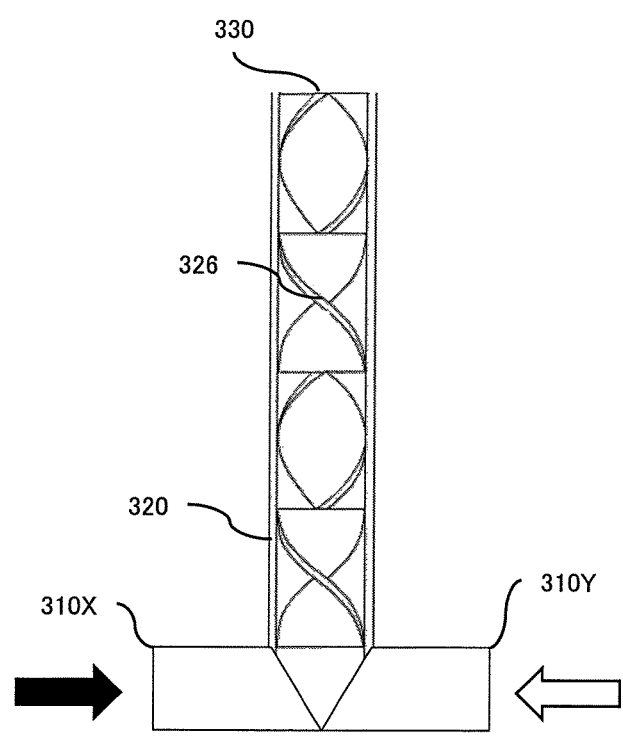
FIG. 16 is a front view of a reaction apparatus using a static mixer in the present invention.

FIG. 16 shows an embodiment of the reaction apparatus using a static mixer in the present invention. In the reaction apparatus, the first inlet flow path (310X) for making a fluid containing glycerin flow into the mixing flow path (320) and the second inlet flow path (310Y) for making a fluid containing supercritical water flow into the mixing flow path (320) are connected to the end of the cylindrical mixing flow path (320). Additionally, in the present embodiment, the mixing flow path (320) is equipped with a static mixer (326). The raw material and the supercritical water made to flow into the mixing flow path (320) are agitated with the static mixer (326) and the interlayer distances are further reduced and hence the miscibility is improved.

Seventh Embodiment

Figure 17:
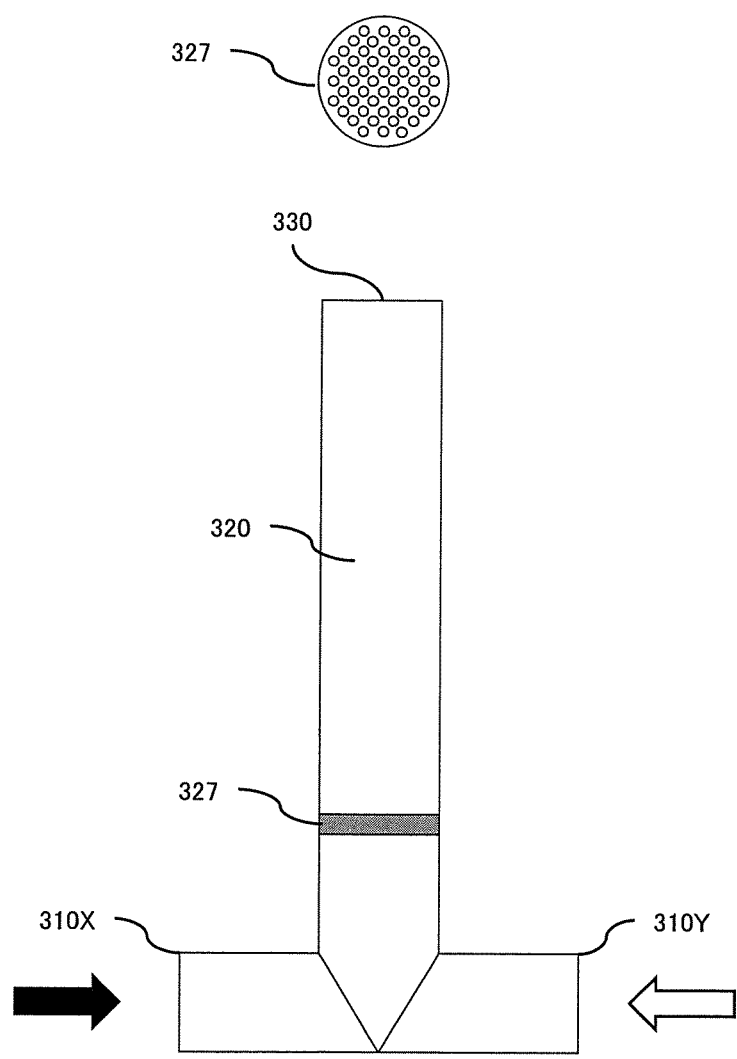
FIG. 17 is a plan view and a front view of a reaction apparatus using a perforated plate in the present invention.

FIG. 17 shows an embodiment of the reaction apparatus using a perforated plate in the present invention. In the reaction apparatus, the first inlet flow path (310X) for making a fluid containing glycerin flow into the mixing flow path (320) and the second inlet flow path (310Y) for making a fluid containing supercritical water flow into the mixing flow path (320) are connected to the end of the cylindrical mixing flow path (320) in the same manner as in the sixth embodiment. Additionally, in the present embodiment, the mixing flow path (320) is equipped with a perforated plate (327). The raw material and the supercritical water made to flow into the mixing flow path (320) are made to pass through the perforated plate (327) to be enhanced in miscibility. The perforated plate (327) may be provided in a plurality of numbers along the mixing flow path (320). In such a case, the perforation rates of the perforated plates may be set at different values from one perforated plate to another.

What is claimed is:

1. A method for synthesizing acrolein by making supercritical water and an acid interact with glycerin, the method comprising:

mixing a fluid comprising glycerin and a fluid comprising supercritical water with each other in a cylindrical mixing flow path;

making the fluid comprising glycerin flow into the mixing flow path from a first inlet flow path, disposed offset from the central axis of the mixing flow path; and making the fluid comprising supercritical water flow into the mixing flow path from a second inlet flow path, disposed offset from the central axis of the mixing flow path, wherein the first inlet flow path and the second inlet flow path are each provided in a plurality of numbers in such a way that the first inlet flow paths and the second inlet flow paths are alternately arranged so as to encircle the central axis of the mixing flow path.

2. A method for synthesizing acrolein by making supercritical water and an acid interact with glycerin, the method comprising:

mixing a fluid comprising glycerin and a fluid comprising supercritical water with each other in a cylindrical mixing flow path;

making the fluid comprising glycerin flow into the mixing flow path from a first inlet flow path, disposed offset from the central axis of the mixing flow path; and making the fluid comprising supercritical water flow into the mixing flow path from a second inlet flow path, disposed offset from the central axis of the mixing flow path, wherein the first inlet flow path and the second inlet flow path are each provided in a plurality of numbers along the flow direction of the mixing flow path so as to be separated away from each other.

3. The method for synthesizing acrolein according to claim 1, wherein a structure is disposed on the central axis of the mixing flow path.

4. The method for synthesizing acrolein according to claim 3, wherein the structure disposed on the central axis of the mixing flow path is formed in such a way that the cross sectional area of the structure is made smaller toward the downstream of the mixing flow path.

5. The method for synthesizing acrolein according to claim 1, wherein between the flow rate QX and the cross sectional area SX per one of the first inlet flow paths and the flow rate QY and the cross sectional area SY per one of the second inlet flow paths, there is a relation represented by the formula (1):

$$QX/SX = QY/SY \qquad (1).$$

6. The method for synthesizing acrolein according to claim 1, wherein the number of the first inlet flow paths is four, and the number of the second inlet flow paths is four.

7. A method for synthesizing acrolein, the method performing the synthesis by carrying out the method according to claim 1 in combination in a plurality of reaction apparatuses.

8. A method for synthesizing acrolein by making supercritical water and an acid interact with glycerin, the method comprising:

mixing a fluid comprising glycerin and a fluid comprising supercritical water with each other in a cylindrical mixing flow path;

making the fluid comprising glycerin flow into the mixing flow path from a first inlet flow path, connected to the mixing flow path; and making the fluid comprising supercritical water flow into the mixing flow path from a second inlet flow path, connected to the mixing flow path, wherein a static mixer is disposed in the mixing flow path.

9. The method for synthesizing acrolein according to claim 8, wherein the number of the first inlet flow paths is four, and the number of the second inlet flow paths is four.

10. A method for synthesizing acrolein by making supercritical water and an acid interact with glycerin, the method comprising:

mixing a fluid comprising glycerin and a fluid comprising supercritical water with each other in a cylindrical mixing flow path;

making the fluid comprising glycerin flow into the mixing flow path from a first inlet flow path, connected to the mixing flow path; and making the fluid comprising supercritical water flow into the mixing flow path from a second inlet flow path, connected to the mixing flow path, wherein a perforated plate is disposed in the mixing flow path.

11. The method for synthesizing acrolein according to claim 10, wherein the number of the first inlet flow paths is four, and the number of the second inlet flow paths is four.

12. A method for synthesizing at least one selected from acrolein, glucose and hydroxymethylfurfural by making at least one of supercritical water and subcritical water interact with a raw material comprising at least one selected from glycerin, cellulose and lignin, the method comprising:

mixing a fluid comprising the raw material and a fluid comprising at least one of supercritical water and subcritical water with each other in a cylindrical mixing flow path;

making the fluid comprising the raw material flow into the mixing flow path from a first inlet flow path, disposed offset from the central axis of the mixing flow path; and making the fluid comprising at least one of supercritical water and subcritical water flow into the mixing flow path from a second inlet flow path, disposed offset from the central axis of the mixing flow path, wherein the first inlet flow path and the second inlet flow path are each provided in a plurality of numbers in such a way that the first inlet flow paths and the second inlet flow paths are alternately arranged so as to encircle the central axis of the mixing flow path.

13. The method for synthesizing acrolein according to claim 12, wherein the number of the first inlet flow paths is four, and the number of the second inlet flow paths is four.

* * * * *